United States Patent [19]

Handler, deceased et al.

[11] Patent Number: 5,005,966
[45] Date of Patent: Apr. 9, 1991

[54] EXOPHTHALMOMETER LIGHT, AND METHODS OF CONSTRUCTING AND UTILIZING SAME

[76] Inventors: Albert W. Handler, deceased, late of West Bloomfield, Mich.; by Bernice Handler, legal representative, West Bloomfield, Mich. 48033; Lawrence F. Handler, North Miami Beach, Fla. 33180

[21] Appl. No.: 201,537

[22] Filed: Jun. 2, 1988

[51] Int. Cl.⁵ .............................................. A61B 3/10
[52] U.S. Cl. ...................................... 351/221; 128/23
[58] Field of Search ............... 351/204, 205, 221, 243; 350/235; 128/23, 18

[56] References Cited

U.S. PATENT DOCUMENTS

| | | | |
|---|---|---|---|
| 3,583,795 | 6/1971 | Heine | 351/16 |
| 3,745,993 | 7/1973 | Feinbloom | 128/23 |
| 3,870,470 | 11/1974 | Dederer et al. | 351/6 |
| 4,265,519 | 5/1981 | Pomerantzeff | 351/16 |
| 4,597,030 | 6/1986 | Brody et al. | 128/23 |

FOREIGN PATENT DOCUMENTS 1.583.436  9/1969  France .

OTHER PUBLICATIONS

The American Journal of Ophthalmology, Jun. 1987, pp. 838 and 839, vol. 2, Chapter 21 of *Clinical Ophthalmology*, pp. 15 and 16.

*Primary Examiner*—Paul M. Dzierzynski
*Attorney, Agent, or Firm*—Weintraub, DuRoss & Brady

[57] ABSTRACT

A self-contained light source for attachment to a Hertel-type exophthalmometer. The device requires no structural alteration of the exophthalmometer and allows for variable positioning of the light source on the exophthalmometer. The device is designed to provide the exophthalmometer with hands free illumination of the eye area and the measuring scale to allow the operator use of both hands when measuring exophthalmus.

14 Claims, 1 Drawing Sheet

EXOPHTHALMOMETER LIGHT, AND METHODS OF CONSTRUCTING AND UTILIZING SAME

BACKGROUND OF THE INVENTION

1. Field of the Invention

The present invention relates in general to means for illuminating the exterior of the eye and its surrounding structure during ophthalmological examination and measurement. Specifically, the present invention is directed towards a means for illuminating a Hertel-type exophthalmometer, as seen in *American Journal of Opthalomology*, June 1987.

2. Description of the Relevant Art

There are known various means for illumination of the eye in ophthalmological examination. Such light devices, for example, are disclosed in U.S. Pat. Nos. 3,583,795; 3,847,470; 4,265,519; and French patent number 1,583,436.

U.S. Pat. No. 3,583,795 discloses a form of ophthalmoscope having an elongated light-conducting rod. The light from this rod is directed toward and into the patient's eye by means of a mirror. The light-emitting member disclosed is contained within a handheld ophthalmoscope and is used principally for an examination of the interior of the eye, rather than for a light source for examination of the external eye area providing sufficient reflected light to illuminate the measuring scale of an exophthalmometer.

U.S. Pat. No. 3,847,470 discloses an indirect binocular ophthalmoscope having a single prism and lens system connected to an illuminating arrangement contained internally within the ophthalmoscope, and having a motor driven cooling air ventilator located in a single lamp housing. The disclosed device is directed towards illumination of the interior of the eye with a hand held binocular ophthalmoscope, with the light emitting means being contained within the ophthalmoscope. Thus, the disclosed invention is not suitable for attachment to a Hertel-type exophthalmometer without structural modification of the exophthalmometer.

French Patent 1,583,436 discloses an ophthalmoscope having an internally-situated light-emitting means consisting of light-carrying fiber optic material arranged around a contact lens for illuminating and viewing of the interior of the eye. The disclosed ophthalmoscope is therefore not suitable for illuminating the exterior portion of the eye, and would require structural modification of the exophthalmometer in use therewith.

U.S. Pat. No. 4,265,519 discloses a wide angle indirect ophthalmoscope along the lines of the above-mentioned French patent, including optical fibers built into a contact lens for the viewing of the interior of the eye. The disclosed invention is therefore not directed towards producing sufficient illumination for the exterior of the eye area, and is drawn towards the reduction of reflected illuminating light rather than the production of reflected illuminating light off of the eye surface as in the present invention.

Thus, it can be seen that the relevant art is fundamentally different in purpose, structure and function from the presently disclosed invention.

It is customary in an ophthalmological examination to measure the protrusion of the eyeballs, i.e. exophthalmos, from their surrounding sockets, i.e., orbits, by taking a measurement of the distance from the lateral rim of the orbit to the apex of the cornea. After such measurement is taken, the value may be compared between each eye and compared to normal values for indications of pathology.

These measurements are most often taken with a Hertel-type exophthalmometer. The Hertel-type exophthalmometer is a device for measuring the protrusion of both eyes with one examination. The Hertel-type exophthalmometer is placed before the patient's face and a reflected image of the eye from lateral orbital rim to the apex of the cornea is cast upon a forward facing measuring scale enabling the operator to obtain a measurement of this lateral distance from a frontal observation. However, normal room lighting is often insufficient to fully illuminate the patient's eye area and thereby reflectively illuminate the exophthalmometer's measuring skill. This lack of illumination can result in inaccurate measurement of eye protrusion.

In the past, various sources of additional lighting have been used with the exophthalmometer. These past forms of additional lighting have suffered from either a lack of ability to be concentrated on the area under examination, as with increased indirect lighting, or required a use of the operators hand to direct the light source, thus requiring the removal of the operator's hand from the exophthalmometer, leading to unsteady placement of the exophthalmometer.

While many lighting devices are known and used in ophtholmological examination, ranging from complex fiber optic devices to a simple hand held flashlight, none have been adapted to provide a point specific light source to allow the measurer to use both hands when utilizing the Hertel-type, exophthalmometer until the current invention.

SUMMARY OF THE INVENTION

The present invention provides a lighting apparatus for selective attachment to and detachment from an external device, and a means for supplYing electrical energy. It includes an illuminating means, and a flexible means for mechanically, electrically and operably connecting the illuminating means to the energy means. A first attachment means is secured to a first predetermined portion of the energy means and a second attachment means is secured to a first predetermined portion of the external device. A third attachment means is secured to a first predetermined portion of the flexible means, and a fourth attachment means is secured to a second predetermined portion of the external device. The energy means may be selectively attached to and detached from desired portions of the external device by selective engagement and disengagement of the first and second attachment means.

The illuminating means may be selectively oriented with respect to and attached to and detached from the second predetermined portion of the external device by selective engagement and disengagement of the third and fourth attachment means.

The primary object of the invention is to provide an add-on light source suitable for use with an ordinary Hertel-type exophthalmometer to increase the accuracy of the readings. Toward that end, this invention is of properly small size for attachment to, and easy manipulation of, the exophthalmometer. Its basic components are a small battery pack and a light bulb at the end of a flexible casing. The invention is designed to attach to the exophthalmometer with no structural modification thereof and no interference with the measuring function.

Another object of the present invention is to provide a device that will provide adequate reflected light from the cornea of sufficient intensity to illuminate the meter's measuring scale for easy reading without undue discomfort to the patient. Using an ordinary, unilluminated, Hertel-type exophthalmometer may lead to inaccurate readings due to difficulty in seeing the unilluminated eye region against the exophthalmometer's scale. This invention uses a lightbulb of sufficient intensity to provide adequate reflected light from the cornea to illuminate the exophthalomometer's scale but not cause discomfort to the patient.

Another object of the invention is to allow the operator full use of both hands when operating the exophthalmometer. Toward that end, the disclosed invention attaches completely to the exophthalmometer to allow free use of both the operator's hands.

Another object of the invention is to provide an adjustably point-specific exophthalmometer light source that is adjustable to illuminate either eye measured and to accommodate different sizes and shapes of patients' faces. Towards that end, the lighting means disclosed is removably fixedly attached to the bridge of the exophthalmometer.

The illuminating device of this invention comprises two basic components; a lightweight electrical supply source and an attached flexible light source-carrying member; which are fitted with means for removably securing these members to the exophthalmometer. The entire illuminating device is lightweight and does not interfere with manipulation of the exophthalmometer The flexible light source-carrying member may be variably positioned along the bridge of the exophthalmometer to provide point specific illumination.

Once the illuminating device members are properly positioned and attached the operator has free use of both hands to position and steady the exophthalmometer for an accurate reading. The operator has then only to turn on power to the light source and take his/her reading.

DETAILED DESCRIPTION OF THE PREFERRED EMBODIMENTS

Figure 1:
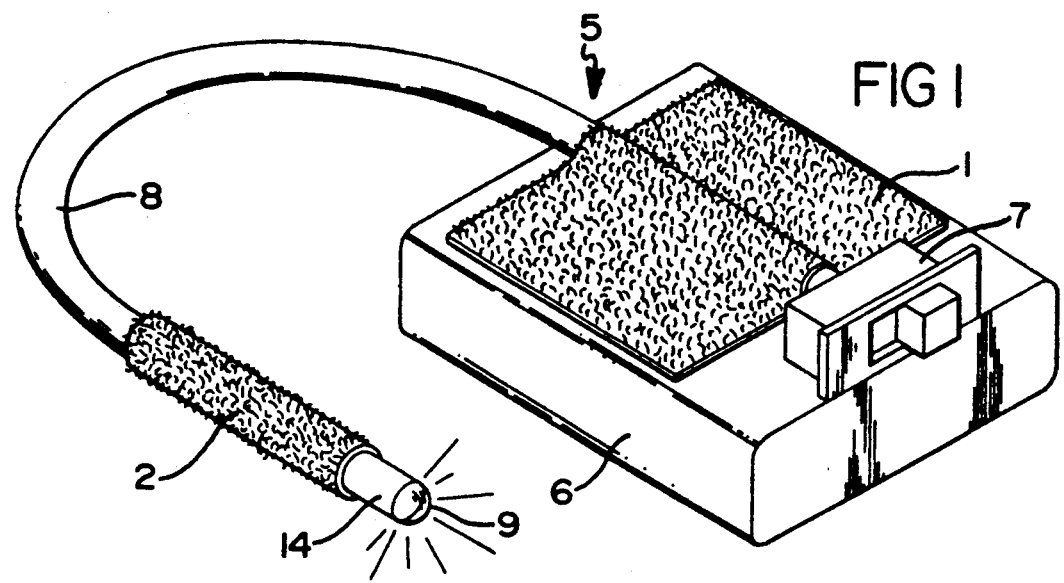
FIG. 1 shows the illuminating device of the disclosed invention.

Referring now to FIG. 1, the illuminating device 5 of the present invention is shown in a preferred embodiment. The battery compartment 6 is a generally rectangular box suitable for containing electrical storage batteries, (not shown) as a power source for light bulb 9. The preferred embodiment of the invention uses two 1½-volt batteries of the size AAA to power a three-volt light bulb 9.

Figure 2:
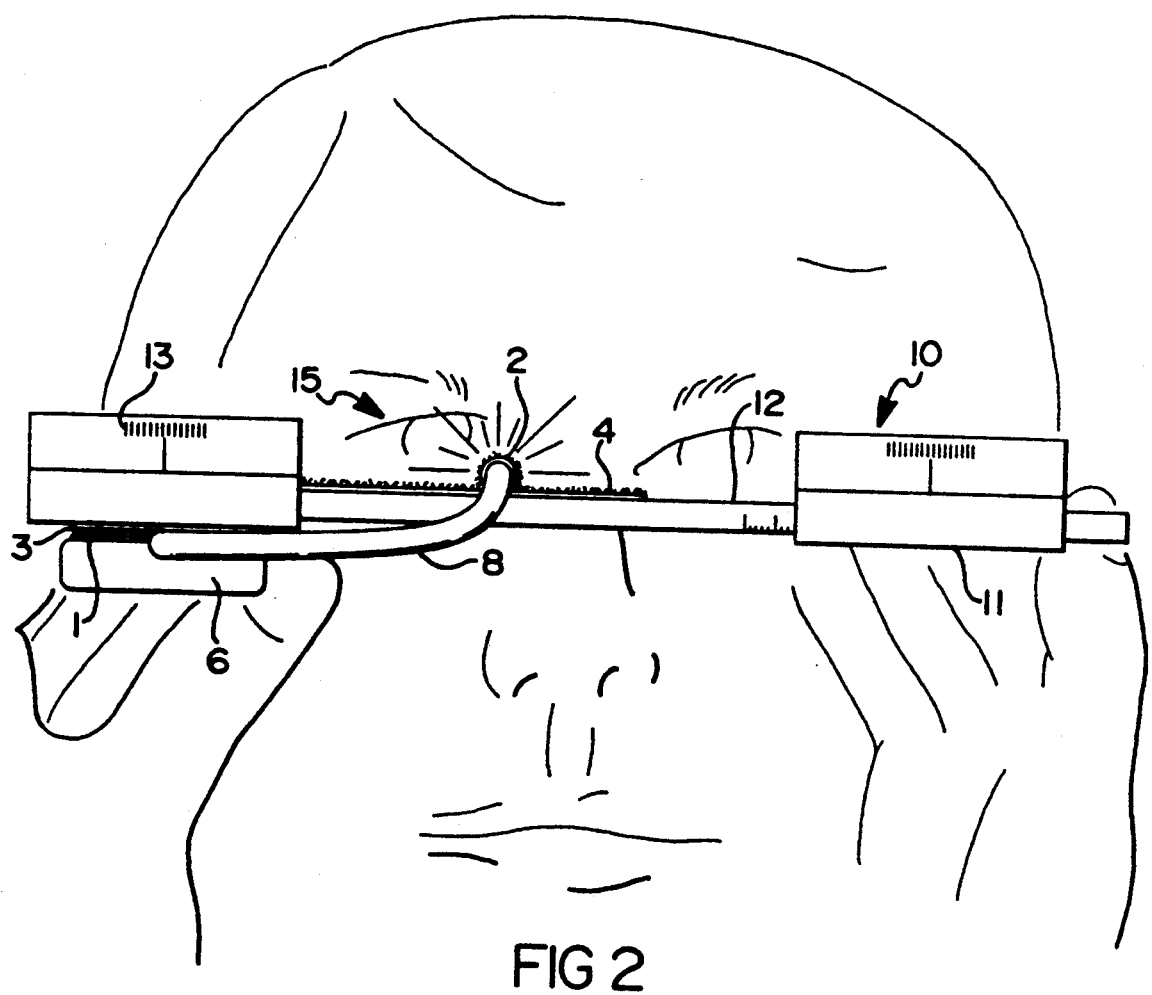
FIG. 2 shows the illuminating device of the disclosed invention secured to a Hertel-type exophthalmometer to which have been added mating attachment strips for the illuminating device. The device and exophthalmometer are shown as they would be placed in front of a patient's face to take a reading.

The battery compartment 6 may be made of any suitable lightweight non-conducting material. The shape of the battery compartment 6 is not limited to be strictly rectangular, but could be variously shaped for easy manipulation, such as having finger grip indentations. The more important criteria for this member is light weight, with one flat upper surface on which to secure an attachment means 1 for mating with a correlative attachment means 3 on the underside 11 of an exophthalmometer 10 (FIG. 2). The preferred method shown uses opposing strips of synthetic fabric type fastening material, commonly known as "VELCRO", thus eliminating the need for structural modification of the exophthalmometer 10. The electrical circuit of the illuminating device 5 preferably, but not necessarily, includes a control means 7 for varying the intensity of light emitted from the light bulb 9. In the preferred embodiment this control means may be an ON/OFF switch 7 mounted on the upper surface of the battery compartment 6 at the opposite end from which a flexible casing 8 for the light emitting means attaches to the battery compartment 6.

The electrical circuit of the preferred illuminating device 5 includes wires (not shown) extending from the battery compartment 6 and enclosed in a flexible casing 8. The wires end in a light bulb socket 14 extending from the end of the flexible casing 8. Affixed on that end of the flexible casing 8 distal from the battery compartment 6 and preceding and proximal to the lightbulb socket 14 is an attachment means 2 suitable for anchoring the light emitting end of lightbulb 9 to a bridge 12 of the exophthalmometer 10 and its correlative fastening means 4. The preferred attachment means necessitate no structural changes to the exophthalmometer 10.

Referring now to FIG. 2, the illuminating device 5 is shown attached to the exophthalmometer 10. The battery compartment 6 is affixed to the underside 11 of the exophthalmometer 10 by mating of the respective attachment means 1 and 3. The lightbulb 9 is then positioned over the bridge 12 of the exophthalmometer 10 and their respective attachment means 2 and 4 are mated. Switch 7 is then placed in the ON position for effective illumination of the eye area 15. Reflection of light from the cornea will then illuminate the measuring scale 13 providing for a more accurate measurement.

It will be appreciated that the preferred embodiment shown is merely illustrative of this invention and that variations within the scope of the invention will be readily apparent to those of ordinary skill in the art. Such variations may include substitute attachment means, such as magnets or suction cups or variations of the shape and composition of materials in the illuminating device. Any such variations are intended to be embraced within the appended claims.

We claim:

1. An exophthalmometer light device, comprising:
   an electrical power source;
   an electrical power control means operably interconnected with and controlling said electrical power source;
   said power source having attachment means for affixing said power source to a Hertel-type exophthalmometer;
   a light-emitting means having a flexible arm to locate the light-emitting means distally from said power source; and
   said light-emitting means being electrically connected to said power source;
   whereby said power source and said light emitting means may be affixed to said Hertel-type exophthalmometer, with the intensity of light emitted being controlled by said electrical power control means, thereby providing the operator of said exophthalmometer with sufficient illumination of the eye area and reflected light therefrom, to make an accurate reading, and leaving both hands free to operate said exophthalmometer.

2. The device according to claim 1, wherein: said electrical power source is self-contained.

3. The device according to claim 1, wherein: said electrical power control means includes an ON/-OFF switch.

4. A device according to claim 1, wherein: said light-emitting means comprises an incandescent lightbulb carried at the end of a length of flexible casing.

5. A device according to claim 1, wherein: said electrical power source is removably affixed to said exophthalmometer.

6. The device according to claim 1, wherein: said electrical power source consists of a single or a numerosity of electrical storage batteries of sufficiently low weight to be easily manipulated by single-hand operation.

7. An exophthalmometer light device, comprising:
A. at least one electrical storage battery;
B. a compartment for holding said electrical storage battery having electrical circuit means;
C. a light bulb distally electrically connected to said battery,
D. electrical wiring running from said battery compartment to said light bulb and electrically connected thereto;
E. a switch operatively connected to said compartment electrical circuit means for controlling the intensity of light emanated by said light bulb;
F. exophthalmometer attachment means fixedly connected to said electrical storage battery compartment; and
G. a flexible casing having two ends, covering said wiring to said bulb and fixedly attached to said battery compartment at one end, and covering all but the light emitting portion of said light bulb at the other end, said flexible casing having affixed thereto said exophthalmometer attachment means proximal to said light bulb;
whereby an ordinarily unlit exophthalmometer may be illuminated by means of attaching said battery compartment to the body of said exophthalmometer and placing the light bulb at that portion of said exophthalmometer most suitable to obtaining sufficient reflection of light from the cornea to produce illumination of the exophthalmometer reading scale.

8. The device according to claim 7, including: two electrical storage batteries of the 1.5 volt variety, size AAA.

9. The device according to claim 7, wherein: said light bulb is a-three volt incandescent type.

10. The device according to claim 7, further comprising:
attachment means correlative to the battery compartment attachment means and suitable for affixation to the underside of a Hertel-type exophthalmometer.

11. The device according to claim 7, further comprising:
attachment means correlative to the flexible casing attachment means for affixation of said flexible casing to the bridge of a Hertel-type exophthalmometer along a majority of its length.

12. The device according to claim 7, wherein: said flexible casing is of sufficient length to connect said light bulb to any portion of the bridge of a Hertel-type exophthalmometer while remaining fixedly attached to said battery compartment.

13. The device according to claim 7, further comprising:
a light bulb socket electrically connected to said wiring and contained within said flexible casing, said casing being open over said light bulb socket void to allow for insertion of said bulb into said socket void.

14. A device to enable an operator to measure eyeball protrusion, comprising:
(a) an exophthalmometer; and
(b) an illuminator, comprising a power source, a power control means operably connected with the power source, the power source having attachment means for affixing the power source to the exophthalmometer, an illuminating means having a flexible arm to locate the light-emitting means distally from the power source; and the light emitting means being electrically connected to the power source, the light emitting means being affixable to the exophthalmometer, the intensity of light emitted by the illuminating means being controlled by the power control means.

* * * * *